US010544186B2

(12) United States Patent
Ignatyev et al.

(10) Patent No.: US 10,544,186 B2
(45) Date of Patent: Jan. 28, 2020

(54) PROCESS FOR THE SYNTHESIS OF AMIDE BONDS WITH THE AID OF NOVEL CATALYSTS

(71) Applicant: Merck Patent GmbH, Darmstadt (DE)

(72) Inventors: Nikolai Mykola Ignatyev, Duisburg (DE); Walter Frank, Wuppertal (DE); Peter Barthen, Rheinberg (DE); Myroslav Vysotsky, Ingelheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 16/348,234

(22) PCT Filed: Nov. 6, 2017

(86) PCT No.: PCT/EP2017/078261
§ 371 (c)(1),
(2) Date: May 8, 2019

(87) PCT Pub. No.: WO2018/087019
PCT Pub. Date: May 17, 2018

(65) Prior Publication Data
US 2019/0270768 A1    Sep. 5, 2019

(30) Foreign Application Priority Data
Nov. 9, 2016 (EP) .................................... 16197873

(51) Int. Cl.
*C07D 207/404* (2006.01)
*C07D 213/89* (2006.01)
*C07D 249/18* (2006.01)
*C07D 263/08* (2006.01)
*C07D 403/14* (2006.01)
*C07D 471/04* (2006.01)
*C07F 9/535* (2006.01)
*C07F 9/6518* (2006.01)
*C07F 9/6561* (2006.01)
*C07K 1/10* (2006.01)
*C07D 253/08* (2006.01)
*C07K 5/065* (2006.01)

(52) U.S. Cl.
CPC ............ *C07K 1/10* (2013.01); *C07D 207/404* (2013.01); *C07D 213/89* (2013.01); *C07D 249/18* (2013.01); *C07D 253/08* (2013.01); *C07D 403/14* (2013.01); *C07D 471/04* (2013.01); *C07F 9/535* (2013.01); *C07F 9/6561* (2013.01); *C07F 9/65188* (2013.01); *C07K 5/06078* (2013.01)

(58) Field of Classification Search
CPC ............ C07D 207/404; C07D 213/88; C07D 249/18; C07D 263/08; C07D 403/14; C07D 471/04; C07F 9/65188; C07F 9/6561; C07K 1/10; C07K 5/06078

USPC ............................. 568/16; 562/808; 564/123
See application file for complete search history.

(56) References Cited

U.S. PATENT DOCUMENTS 7,094,328 B2    8/2006  Ignatyev et al.
2013/0023661 A1  1/2013  Ignatyev et al.

FOREIGN PATENT DOCUMENTS

WO      03002579 A1    1/2003
WO     2011124307 A1   10/2011

OTHER PUBLICATIONS

International Search Report PCT/EP2017/078261 dated Jan. 19, 2019 (pp. 1-3).
A. El-Faham, Chem. Lett., 1998, pp. 671-672.
A. K. Saha; P. Schultz; H. Rapoport, J. Am. Chem. Soc., vol. 111, 1989, pp. 4856-4859.
Anderson, G. W.; Paul, R., J. Am. Chem. Soc., vol. 80, 1958, pp. 4423.
F. Albericio; J. M. Bofill; A. El-Faham; S. A. Kates, J. Org. Chem., vol. 63, 1998, pp. 9678-9683.
F. S. Gibson; H. Rapoport, J. Org. Chem., vol. 60, 1995, pp. 2615-2617.
B. Castro; J. R. Dormoy; G. Evin; C. Selve, Tetrahedron Lett., vol. 14, 1975, pp. 1219-1222.
F. Albericio; M. Cases; J. Alsina; S. A. Triolo; L. A. Carpino; S. A. Kates, Tetrahedron Lett., vol. 38, 1997, pp. 4853-4856.
I. Krossing; I. Raabe, Angew. Chem., vol. 116, 2004, pp. 2116-2142.
B. Weinstein; A. E. Pritchard, J. Chem. Soc., 1972, pp. 1015.
L. A. Carpino; H. Imazumi; A. El-Faham; F. J. Ferrer; C. W. Zhang; Y. S. Lee; B. M. Foxman; P. Henklein; C. Hanay; C. Mugge, Angew. Chem. Int. Ed., vol. 41, 2002, pp. 442-445.
P. Li; J. C. Xu, Tetrahedron, vol. 56, 2000, pp. 4437-4445.
P. Li; J. C. Xu, J. Pept. Res., vol. 58, 2001, pp. 129-139.
J. Coste; D. Le-Nguyen; B. Castro, Tetrahedron Lett., vol. 31, 1990, pp. 205-208.
T. Hoeg-Jensen; C. E. Olsen; A. Holm, J. Org. Chem., vol. 59, 1994, pp. 1257-1263.
L. A. Carpino; A. Elfaham, J. Am. Chem. Soc., vol. 117, 1995, pp. 5401-5402.
L. Spanier; E. Ciglia; F. K. Hansen; K. Kuna; W. Frank; H. Gohlke; T. Kurz, J. Org. Chem., vol. 79, 2014, pp. 1582-1593.
M. Uyanik; D. Nakashima; K. Ishihara, Angew. Chem., vol. 124, 2012, pp. 9227-9230.
V. Dourtoglou; J.-C. Ziegler; B. Gross, Tetrahedron Lett., vol. 15, 1978, pp. 1269-1272.

(Continued)

*Primary Examiner* — Venkataraman Balasubramanian
(74) *Attorney, Agent, or Firm* — Millen White Zelano & Branigan, PC

(57) ABSTRACT

The invention relates to a process for the production of amide bonds, in particular peptide bonds, with the aid of novel amide linking reagents containing an anion of the formula (I), to the novel reagents, and to the preparation thereof.

7 Claims, No Drawings

(56) References Cited

OTHER PUBLICATIONS

R. Knorr; A. Trzeciak; W. Bannwarth; D. Gillessen, Tetrahedron Lett., vol. 30, 1989, pp. 1927-1930.
L. A. Carpino; A. El-Faham, J. Org. Chem., vol. 59, 1994, pp. 695-698.

PROCESS FOR THE SYNTHESIS OF AMIDE BONDS WITH THE AID OF NOVEL CATALYSTS

The invention relates to a process for the production of amide bonds, in particular peptide bonds, with the aid of novel amide linking reagents as catalysts, to the novel reagents, and to the preparation thereof.

Modern standard processes for peptide synthesis use effective peptide linking reagents. The formation of amide bonds is likewise of importance for the synthesis of other organic molecules, for example in the synthesis of the compounds atorvastatin, lisinopril or diltiazem. An amide bond is formed by reaction of an acid with a primary or secondary amine in the presence of a base and with the aid of an amide linking reagent. Peptide synthesis is, described in simplified terms, a reaction between an amino acid and a primary or secondary amine in the presence of one equivalent of peptide linking reagent and two equivalents of tertiary amine (as proton acceptor) in two steps. The first step is activation of an N-protected amino acid to give the active ester, which reacts virtually immediately in the second step with a carboxyl-protected amino acid (amine) to give the amide. The amide linking reagents or peptide linking reagents have one or more functional groups which serve not only for activation of a carboxyl group, but also for elimination of one equivalent of water.

The history of peptide linking reagents begins with carbodiimides which carry only one carbodiimide group. Dicyclohexylcarbodiimide, for example, has been investigated since 1955 and reacts in the first step with a carboxylic acid to give an O-acylurea, which reacts with the amine by means of its very active ester group and forms one equivalent of urea, which can normally easily be separated off. However, it has been found that on the one hand N-acylurea forms as byproduct, and on the other hand peptide linking reactions of this type generally proceed with strong epimerisation (racemisation, configuration reversal). More modern peptide linking reagents allow the linking of one equivalent of acid and one equivalent of amine with a much lower degree of epimerisation and carry a positively charged group which reacts during the reaction to give, for example, urea or phosphorus oxide, and a neutral group, which serves only for activation of an acid group. Efficient peptide linking reagents of this type are in the form of organic salts, for example uronium [F. Albericio, J. M. Bofill, A. El-faham, S. A. Kates, *J. Org. Chem.* 1998, 63, 9678-9683], aminium [L. A. Carpino, H. Imazumi, A. El-faham, F. J. Ferrer, C. W. Zhang, Y. S. Lee, B. M. Foxman, P. Henklein, C. Hanay, C. Mugge, H. Wenschuh, K. Klose, M. Beyermann, M. Bienert, *Angew. Chem. Int. Ed.* 2002, 41, 442-445], immonium (or carbonium) [P. Li, J. C. Xu, *Tetrahedron* 2000, 56, 4437-4445] [P. Li, J. C. Xu, *J. Pept. Res.* 2001, 58, 129-139], imidazolium [Anderson, G. W.; Paul, R. *J. Am. Chem. Soc.* 1958, 80, 4423] [A. K. Saha, P. Schultz, H. Rapoport, *J. Am. Chem. Soc.* 1989, 111, 4856-4859] [F. S. Gibson, H. Rapoport, *J. Org. Chem.* 1995, 60, 2615-2617] or phosphonium salts [B. Castro, J. R. Dormoy, G. Evin and C. Selve, *Tetrahedron Lett.* 1975, 14, 1219-1222] [F. Albericio, J. M. Bofill, A. El-Faham and S. A. Kates, *J. Org. Chem.* 1998, 63, 9678-9683] [J. Coste, D. Le-Nguyen, B. Castro, *Tetrahedron Lett.* 1990, 31, 205-208] [F. Albericio, M. Cases, J. Alsina, S. A. Triolo, L. A. Carpino, S. A. Kates, *Tetrahedron Lett.* 1997, 38, 4853-4856] [T. HoegJensen, C. E. Olsen and A. Holm, *J. Org. Chem.* 1994, 59, 1257-1263]. More recent fluorouronium peptide linking reagents utilise the formation of acid fluorides in the reaction with amino acids. Fluoro-N,N,N',N'-tetramethylformamidinium hexafluorophosphate (TFFH) and bis(tetramethylene)fluoroformamidinium hexafluorophosphate (BTFFH) are employed particularly effectively here [L. A. Carpino, A. Elfaham, *J. Am. Chem. Soc.* 1995, 117, 5401-5402] [A. El-Faham, *Chem. Lett.* 1998, 671-672].

The most recent and widely investigated peptide linking reagents are employed as non-explosive replacement for benzotriazole derivatives, for example ethyl (hydroxyimino) cyanoactetate (Oxyma) and, with the additional advantage of the positive influence of a morpholine substituent, (1-cyano-2-ethoxy-2-oxoethylideneaminooxy)dimethylaminomorpholino-carbenium hexafluorophosphate (COMU) [L. Spanier, E. Ciglia, F. K. Hansen, K. Kuna, W. Frank, H. Gohlke, T. Kurz, *J. Org. Chem.* 2014, 79, 1582-1593].

Of particular current interest here is the behaviour of the amide linking reagents, in particular the peptide linking reagents, in solution. The counterions of the reagents currently employed are generally tetrafluoroborate or hexafluorophosphate. The solubility of the amide linking reagents known to date for the production of amide bonds in organic solvents is still unsatisfactory or the choice of a suitable solvent for the desired synthesis of the amide bond is often restricted, which generally leads to low conversion rates in the reaction.

For example, it is known from the prior art that a fluorination can be influenced by the choice of different anions in the fluorinating reagent. WO 2011/124307 describes that fluorinating reagents containing perfluoroalkylfluorophosphate anions exhibit advantageous properties with respect to their solubility, stability and reactivity compared with fluorinating reagents containing other anions. The anion appears to be of crucial importance in this reaction. It is thought that the strength of the electrostatic interaction between anion and cation also influences the reactivity of the cation here, as has likewise been described for some other reactions [I. Krossing, I. Raabe, *Angew. Chem.* 2004, 116, 2116-2142] [M. Uyanik, D. Nakashima, K. Ishihara, *Angew. Chem.* 2012, 124, 9227-9230].

To date, however, no significant differences in reactivity have been observed for peptide linking reagents having the same cation and different anions [V. Dourtoglou, J.-C. Ziegler, B. Gross, *Tetrahedron Lett.* 1978, 15, 1269-1272] [R. Knorr, A. Trzeciak, W. Bannwarth, D. Gillessen, *Tetrahedron Lett.* 1989, 30, 1927-1930].

As can be seen in the general scheme with the example of O-(3,4-dihydro-4-oxo-1,2,3-benzotriazin-3-yl)-N,N,N',N'-tetramethyluronium tetrafluoroborate (TDBTU) as amide linking reagent, there are several steps in the acid activation:

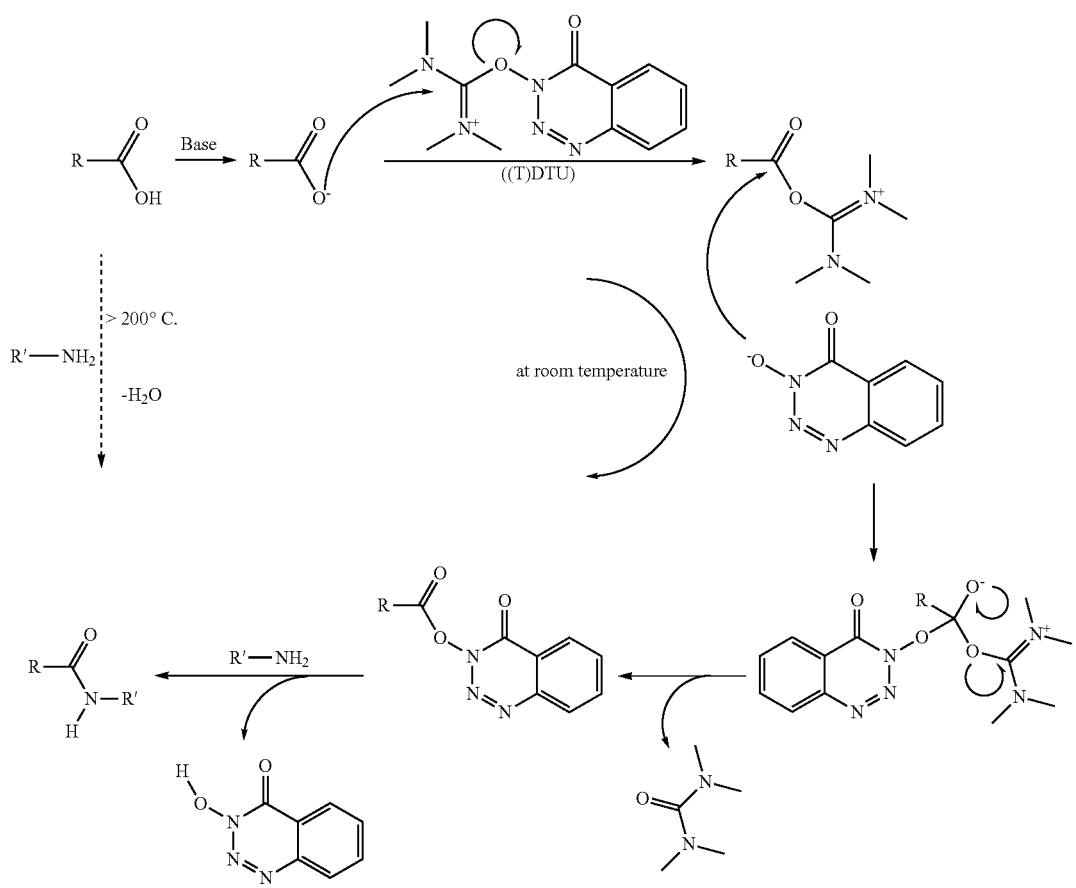

The carboxylic acid (RCOOH) is firstly deprotonated by the base, and the anion formed subsequently reacts with the cation of the amide linking reagent. The anion formed then attacks the carbonyl carbon of the carboxylic acid, with formation of a molecule of tetramethylurea and an active ester, which reacts with the amine (R'—NH$_2$) to give the amide (R—C(O)—NH—R'). In this reaction, two steps proceed for which the reactivity of the positively charged groups plays a crucial role. In order to improve the reactivity, the weakest possible coordination of the cation of the amide linking reagent to the counterion has proven important, i.e. the use of weakly coordinating anions is advantageous.

Under ideal conditions, the coupling reaction for the amide bonding should proceed at a high rate without racemisation and side reactions and in high yield with use of equimolar amounts of carboxyl and amino component.

There continues to be a need for novel amide linking reagents which come as close as possible to these ideal conditions and offer the person skilled in the art of synthesis greater flexibility in the correct choice of reagents and reaction conditions.

The object of the present invention was thus the provision of alternative amide linking reagents having improved properties, for example with respect to their cation-anion interaction, solubility and/or reactivity. In particular, the aim is for this to lead to increased variability regarding suitable solvents for the amide linking reaction. It is likewise an object of the invention to accelerate the amide bond formation and/or to increase the conversion rates and yield.

Surprisingly, it has now been found that amide linking reagents containing perfluoroalkylfluorophosphate anions achieve this object.

The novel compounds exhibit significantly higher solubility in many organic solvents, particularly in dichloromethane, acetonitrile, tetrahydrofuran (THF), dimethylformamide (DMF) or mixtures thereof, than the corresponding tetrafluoroborates or hexafluorophosphates. This improved solubility enables high variability of suitable solvents for the desired use in the amide linking reaction. The novel reagents therefore also enable the linking together of acids and amides which were hitherto unable to react in the standard solvents or only with unsatisfactory yield.

The novel amide linking reagents containing perfluoroalkylfluorophosphate anions can furthermore be generated in situ from corresponding amide linking reagents containing the [BF$_4$] or [PF$_6$] anion and metathesis with a corresponding potassium or sodium perfluoroalkylfluorophosphate.

Investigations of the acid activation of Z-Aib-OH (Z-protected aminoisobutyric acid) as test substance in THF as solvent and in the presence of collidine (TMP) as base in most cases confirm the higher activity of the novel amide linking reagents compared with the analogous hexafluorophosphates and tetrafluoroborates. Z-Aib-OH was selected for the activation experiments since the compound carries a carboxyl group which is not easy to activate and the reaction can easily be followed by means of NMR experiments [L. A. Carpino, A. El-Faham, *J. Org. Chem.* 1994, 59, 695-698].

The syntheses of dipeptides for the example of Ac-Phe-Ala-OMe exhibit higher conversion rates and in some cases lower degrees of epimerisation in the presence of the perfluoroalkylfluorophosphate compounds compared with the analogous hexafluorophosphates and tetrafluoroborates. More detailed explanations are described below in the experimental part.

The advantage of the novel peptide linking reactions is, in particular, the gain in time in the peptide synthesis through faster reaction times.

The invention therefore relates firstly to a process for the production of an amide bond by reaction of an acid with a primary or secondary amine in the presence of a base with the aid of an amide linking reagent, characterised in that use is made of at least one amide linking reagent containing an anion of the formula (I), $$[P(C_nF_{2n+1})_yF_{6-y}]^- \qquad (I)$$

where n stands on each occurrence, independently, for 1, 2, 3, 4, 5, 6, 7 or 8 and y stands for 1, 2, 3 or 4.

The anion of the formula (I) can also be described with the abbreviation $FAP^-$.

In a preferred embodiment of the process, use is made of amide linking reagents in which the variable n in the anion of the formula (I) stands on each occurrence, independently, for the integer 2, 3 or 4. Accordingly, preference is given to perfluoroalkylfluorophosphate anions of the formula (I) in which the perfluoroalkyl groups each have, independently of one another, 2, 3 or 4 C atoms. The perfluoroalkyl group in the anions of the formula (I) is particularly preferably identical. Suitable perfluoroalkyl groups having 2 to 4 C atoms are accordingly pentafluoroethyl, n- or iso-heptafluoropropyl and n-, sec-, iso- or tert-nonafluorobutyl.

The invention therefore furthermore relates to the process, as described above, in which use is made of amide linking reagents containing anions of the formula (I) in which the variable n stands on each occurrence, independently, for 2, 3 or 4.

Preferred anions of the formula (I) can be selected from the group of the anions $[(C_2F_5)_3PF_3]^-$, $[(C_3F_7)_3PF_3]^-$, $[(C_4F_9)_3PF_3]^-$, $[(C_2F_5)_2PF_4]^-$, $[(C_3F_7)_2PF_4]^-$, $[(C_4F_9)_2PF_4]^-$, $[(C_2F_5)PF_5]^-$, $[(C_3F_7)PF_5]^-$ and $[(C_4F_9)PF_5]^-$. The perfluoroalkyl groups in the anion of the formula (I) are preferably straightchain. Very particularly preferred anions of the formula (I) are $[(C_2F_5)_3PF_3]^-$ and $[(n-C_4F_9)_3PF_3]^-$.

The invention therefore furthermore relates to the process, as described above, in which use is made of amide linking reagents containing anions of the formula (I) in which the anion (I) is selected from the group $[(C_2F_5)_3PF_3]^-$, $[(C_3F_7)_3PF_3]^-$, $[(C_4F_9)_3PF_3]^-$, $[(C_2F_5)_2PF_4]^-$, $[(C_3F_7)_2PF_4]^-$, $[(C_4F_9)_2PF_4]^-$, $[(C_2F_5)PF_5]^-$, $[(C_3F_7)PF_5]^-$ and $[(C_4F_9)PF_5]^-$.

The cation of the amide linking reagents is not restricted here, but instead encompasses all cations which are able to react with the corresponding acid in the process according to the invention and correspondingly activate the latter.

Preferred cations of the amide linking reagents in the process according to the invention are selected from the group uronium, thiouronium, guanidinium, aminium, carbonium, imidazolium and phosphonium cations.

The invention therefore furthermore relates to the process, as described above or described as preferred, in which the cation of the amide linking reagent is a uronium, thiouronium, guanidinium, aminium, carbonium, imidazolium or phosphonium cation.

The process according to the invention is preferably a process for the preparation of peptides and the amide linking reagent described is preferably a peptide linking reagent.

The invention therefore furthermore relates to the process as described above or preferably described, in which a peptide bond is produced.

Preferred amide linking or peptide linking reagents are derived from known peptide linking reagents, but where, in accordance with the invention, the anion is replaced by a perfluoroalkylfluorophosphate anion.

Known peptide reagents are

BTFFH meaning bis(tetramethylene)fluoroformamidinium hexafluorophosphate,

BOP meaning (benzotriazol-1-yloxy)tris(dimethylamino) phosphonium hexafluorophosphate, COMU meaning (1-cyano-2-ethoxy-2-oxoethylideneaminooxy)dimethylaminomorpholinocarbenium hexafluorophosphate, HATU meaning 1-(dimethylamino(dimethylamonium-1-ylidene)methyl)-1H-azabenzo[d][1,2,3] triazole 3-oxide hexafluorophosphate (known commercially as O-(7-azabenzotriazol-1-yl)-N,N,N',N'-tetramethyluronium hexafluorophosphate), HBPyU meaning 1-(pyrrolidino(pyrrolidinium-1-ylidene)methyl)-1H-benzo-[d][1,2,3]triazole 3-oxide hexafluorophosphate (known commercially as O-(benzotriazol-1-yl)-N,N,N',N'-bis(tetramethylene)uronium hexafluorophosphate), HBTU meaning 1-(dimethylamino(dimethylamonium-1-ylidene)methyl)-1H-benzo[d][1,2,3]triazole 3-oxide hexafluorophosphate (known commercially as O-(benzotriazol-1-yl)-N,N,N',N'-tetramethyluronium hexafluorophosphate), HOTT meaning S-(1-oxido-2-pyridyl)-N,N,N',N'-tetramethylthiouronium hexafluorophosphate, PfTU meaning O-pentafluorophenyl-N,N,N',N'-tetramethyluronium hexafluorophosphate, PyAOP meaning (7-azabenzotriazol-1-yloxy)tris(pyrrolidino)phosphonium hexafluorophosphate, PyBOP meaning (benzotriazol-1-yloxy)tris(pyrrolidino) phosphonium hexafluorophosphate, TDBTU meaning O-(3,4-dihydro-4-oxo-1,2,3-benzotriazin-3-yl)-N,N,N',N'-tetramethyluronium tetrafluoroborate, TFFH meaning fluoro-N,N,N',N'-tetramethylformamidinium hexafluorophosphate, TSTU meaning O—(N-succinimidyl)-N,N,N',N'-tetramethyluronium tetrafluoroborate.

The following compounds are therefore particularly preferably used as amide linking reagent or peptide linking reagent in the process according to the invention, as described above, where $FAP^-$ stands for the anion of the formula (I), as described above:

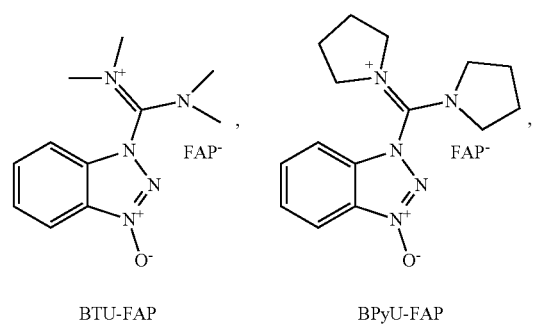

BTU-FAP          BPyU-FAP

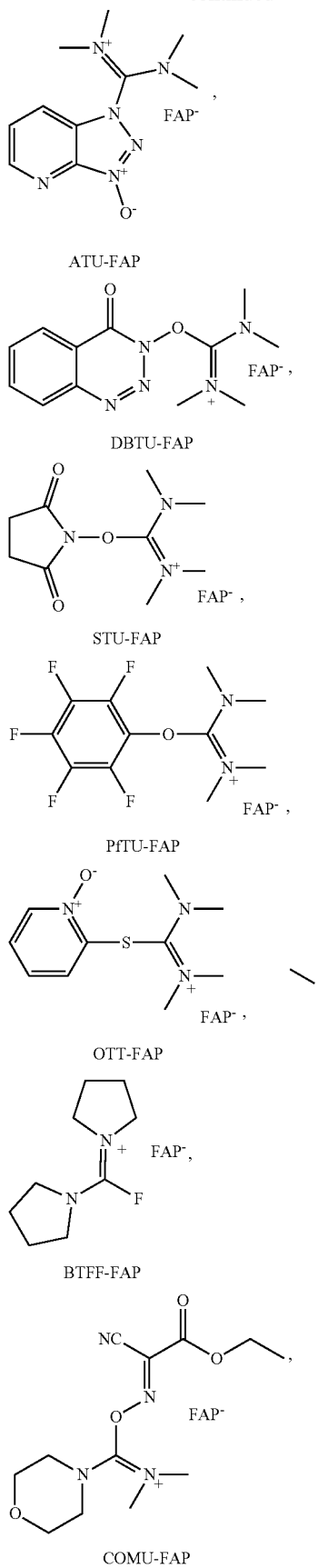

ATU-FAP

DBTU-FAP

STU-FAP

PfTU-FAP

OTT-FAP

TFF-FAP

BTFF-FAP

COMU-FAP

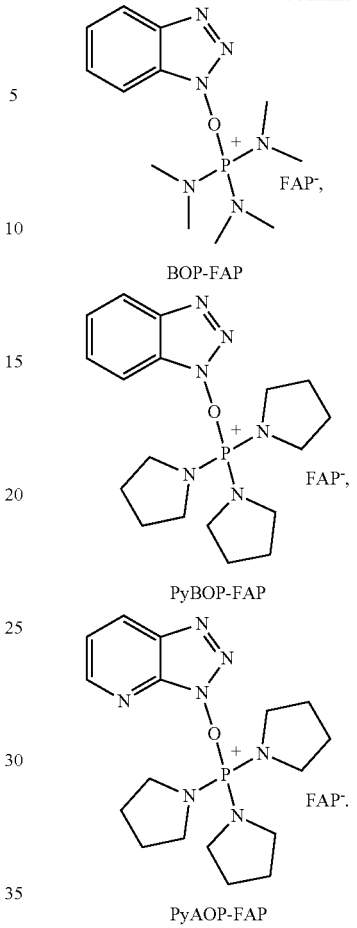

BOP-FAP

PyBOP-FAP

PyAOP-FAP

In the process according to the invention, as described above, the compounds BTU-FAP, BPyU-FAP, ATU-FAP, DBTU-FAP, STU-FAP, PfTU-FAP, OTT-FAP, TFF-FAP, BTFF-FAP, COMU-FAP, BOP-FAP, PyBOP-FAP or PyAOP-FAP are therefore very particularly preferably used as amide linking reagent or peptide linking reagent, where FAP⁻ stands for a preferred anion of the formula (I), as described above, in particular for $[(C_2F_5)_3PF_3]^-$, $[(C_3F_7)_3PF_3]^-$, $[(C_4F_9)_3PF_3]^-$, $[(C_2F_5)_2PF_4]^-$, $[(C_3F_7)_2PF_4]^-$, $[(C_4F_9)_2PF_4]^-$, $[(C_2F_5)PF_5]^-$, $[(C_3F_7)PF_5]^-$ and $[(C_4F_9)PF_5]^-$ or very particularly preferably for $[(C_2F_5)_3PF_3]^-$ and $[(n-C_4F_9)_3PF_3]^-$.

From the group of the amide linking reagents BTU-FAP, BPyU-FAP, ATU-FAP, DBTU-FAP, STU-FAP, PfTU-FAP, OTT-FAP, TFF-FAP, BTFF-FAP, COMU-FAP, BOP-FAP, PyBOP-FAP and PyAOP-FAP, particular preference is given to the amide linking reagents BTU-FAP, BPyU-FAP, ATU-FAP, DBTU-FAP, STU-FAP, PfTU-FAP, OTT-FAP, TFF-FAP, BTFF-FAP, COMU-FAP and BOP-FAP, where FAP⁻ stands for an anion of the formula (I), as described above or preferably described.

The invention furthermore relates to the compounds BTU-FAP, BPyU-FAP, ATU-FAP, DBTU-FAP, STU-FAP, PfTU-FAP, OTT-FAP, TFF-FAP, BTFF-FAP, COMU-FAP, BOP-FAP, PyBOP-FAP and PyAOP-FAP,

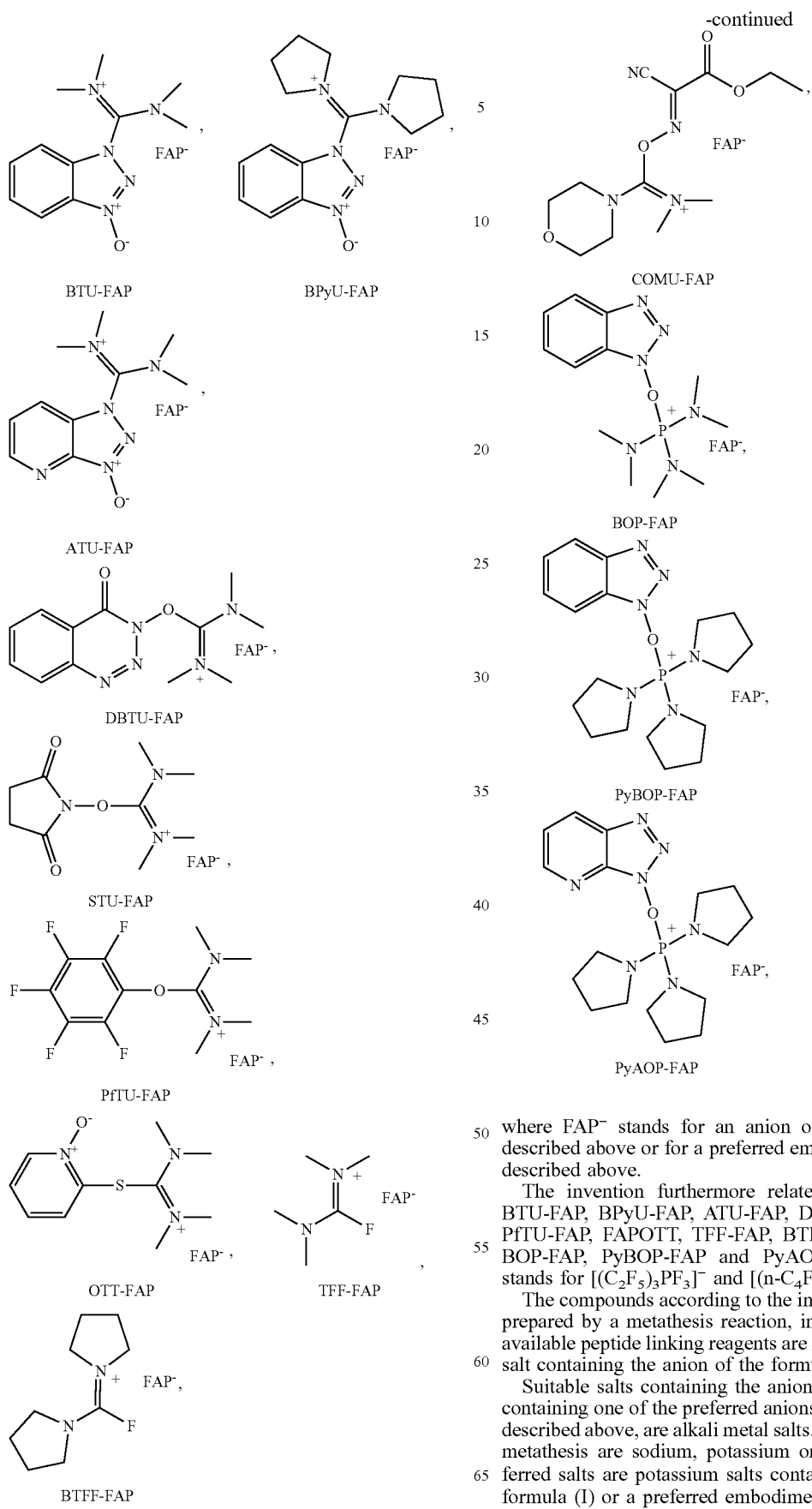

where FAP⁻ stands for an anion of the formula (I), as described above or for a preferred embodiment of FAP⁻, as described above.

The invention furthermore relates to the compounds BTU-FAP, BPyU-FAP, ATU-FAP, DBTU-FAP, STU-FAP, PfTU-FAP, FAPOTT, TFF-FAP, BTFF-FAP, COMU-FAP, BOP-FAP, PyBOP-FAP and PyAOP-FAP, where FAP⁻ stands for [(C$_2$F$_5$)$_3$PF$_3$]⁻ and [(n-C$_4$F$_9$)$_3$PF$_3$]⁻.

The compounds according to the invention are preferably prepared by a metathesis reaction, in which commercially available peptide linking reagents are reacted with a suitable salt containing the anion of the formula (I).

Suitable salts containing the anion of the formula (I) or containing one of the preferred anions of the formula (I), as described above, are alkali metal salts. Preferred salts for the metathesis are sodium, potassium or rubidium salts. Preferred salts are potassium salts containing an anion of the formula (I) or a preferred embodiment of the anion of the formula (I).

Alternatively, the peptide linking reagents, as described above, can be prepared in a two-step synthesis, as shown in the following scheme:

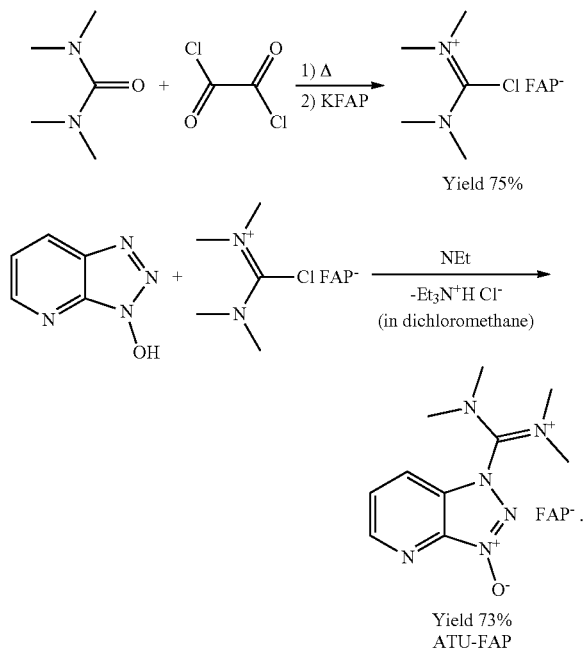

Yield 75%

Yield 73%
ATU-FAP

The metathesis for the preparation of the amide linking reagents, as described above or as preferably described, can be carried out in water or in organic solvents or a mixture of these solvents. The metathesis is preferably carried out in organic solvents, preferably at temperatures between −80° and 100° C., particularly at −30° C. to room temperature. Suitable organic solvents are selected, for example, from acetonitrile, propionitrile, acetone, dioxane, dichloromethane, dimethoxyethane, diethyl ether, methyl t-butyl ether, dimethyl sulfoxide, tetrahydrofuran, dimethylformamide, N,N-dimethylacetamide or alcohol, for example methanol, ethanol or isopropanol. The reaction is preferably carried out in the solvents acetonitrile, propionitrile, acetone, or a mixture of acetonitrile/dichloromethane or acetonitrile/diethyl ether. The reaction is particularly preferably carried out in acetonitrile. Two preferred metathesis methods are described in the experimental part. The work-up is preferably carried out by removal of the organic solvent and subsequent extraction, with insoluble constituents being filtered off, if necessary, before removal of the solvent.

As described above, the choice of acids and primary or secondary amines for the process according to the invention and thus the amide linking reaction is not restricted.

Many starting materials, as described above, are commercially available or are prepared by processes which are known to the person skilled in the art.

Particularly suitable starting materials for the process according to the invention are correspondingly amino acids provided with protecting groups, which can be both the acid and also the primary or secondary amine. The type of amino acid is not restricted here. They can be of natural or synthetic origin.

The corresponding choice of protecting group for the desired amide formation is known to the person skilled in the art of synthesis. A widely used amino protecting group is the benzyloxycarbonyl group, which is also described with the abbreviation "Z". However, acetyl groups, which are often described with the abbreviation "Ac", are also suitable.

The base is likewise not restricted in the process according to invention. Any type of proton acceptor is possible for removing a proton from the acid in the first step, as described above in the general scheme. Many bases, as described above, are commercially available. Preferred bases are tertiary amines. A known example of a tertiary amine which is used as base is 2,4,6-trimethylpyridine, also called collidine or TMP. The base is preferably added in excess, based on the amount of acid. It is preferred to use three equivalents of base, based on one equivalent of the acid. It is furthermore preferred in each case to use one equivalent of amine and one equivalent of the amide linking reagent, as described above.

The further reaction conditions for the amide linking reaction are known to the person skilled in the art of synthesis.

In a preferred embodiment of the process according to the invention, the reaction is carried out in an organic solvent. Any common organic solvent in which the novel amide linking reagents described above and the acid and the amine are sufficiently soluble can be employed for this purpose. Particularly suitable organic solvents are dichloromethane, acetonitrile, tetrahydrofuran (THF), dimethylformamide (DMF) or mixtures thereof in all ratios.

Tetrahydrofuran is particularly preferably employed.

In the process according to the invention, the reaction is preferably carried out at a temperature between −20° C. to 120° C., particularly preferably a temperature of 10° C. to 40° C. The reaction is very particularly advantageously carried out at room temperature. The choice of a suitable reaction temperature can easily be made by the person skilled in the art.

The actual amide bonding reaction can be followed by one purification step(s). Suitable purification steps include separating off readily volatile components by distillation or condensation, extraction with an organic solvent, precipitation by addition of an organic solvent, salt exchange or a combination of these methods. Any known separation or purification method can be used or combined for this purpose.

The following examples explain the present invention greater detail without restricting the scope of protection. In particular, the reaction conditions, features, properties and advantages, described in the examples, of the amide linking reagents on which the relevant examples are based can also be applied to other processes and amide linking reagents that are not explained in detail, but fall within the scope of protection, unless stated otherwise elsewhere. In addition, the invention can be carried out throughout the range claimed and is not restricted to the examples given here.

NMR spectroscopy: NMR samples are measured either in a 5 mm ($Ø_A$) glass NMR tube or a 3.7 mm ($Ø_A$) FEP inliner at 25° C. In the case of measurements in FEP, the inliner is inserted into a 5 mm ($Ø_A$) precision thinglass NMR tube (Wilmad 537). The lock substance, $CD_3CN$, is located in the glass NMR tube, i.e. between glass and FEP inliner, and is denoted below by film measurement or solvent film. The measurements are carried out in a 400 MHz Bruker Avance III spectrometer with a 9.3980 T cryomagnet and a 5 mm BBFO sample head. $^1$H-NMR spectra are measured in the $^1$H/$^{19}$F channel at 400.17 MHz. $^{19}$F- and $^{31}$P-NMR spectra are measured in the broad band channel at 376.54 and 161.99 MHz. The $^1$H-NMR chemical shifts are relative to tetramethylsilane (TMS) and are for the residual proton signals of the solvents $D_2O$ (4.81 ppm), $CDCl_3$ (7.24 ppm)

and CD$_3$CN (1.96 ppm). The $^{19}$F chemical shifts are relative to CFCl$_3$ and are for the internal standards C$_6$F$_6$(−162.9 ppm) or C$_6$H$_5$CF$_3$ (−63.9 ppm). The $^{31}$P chemical shifts are relative to H$_3$PO$_4$ (85%).

EXAMPLES

Method A:

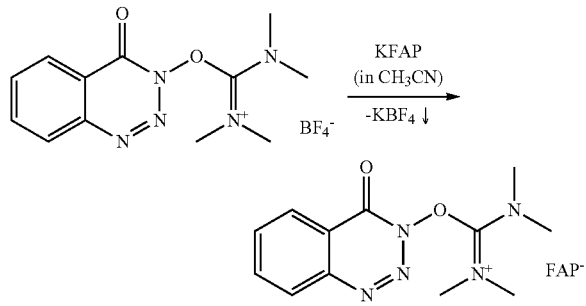

Method B:

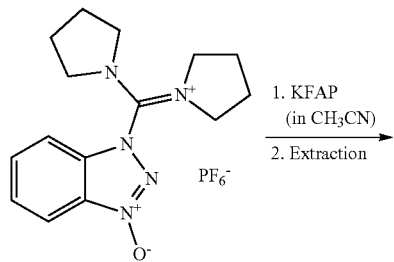

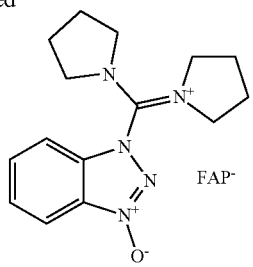

Example A) Synthesis of the Amide Linking Reagents

Method A: Synthesis from Tetrafluoroborates

A solution of potassium tris(pentafluoroethyl)trifluorophosphate, K[(C$_2$F$_5$)$_3$PF$_3$] (4.188 g, 8.65 mmol) in acetonitrile (15 ml) is added to a solution of the amide linking reagent containing tetrafluoroborate anions (8.65 mmol) in acetonitrile (15 ml), and the reaction mixture is stirred at 0° C. in an ice bath for two hours. The resultant mixture is filtered. The residue, principally insoluble potassium tetrafluoroborate, is washed three times with 10 ml of cold acetonitrile, and the washing solutions are combined with mother liquor. The acetonitrile is removed from the combined solutions in vacuo, and the residue (FAP-containing peptide linking reagent) is dried in vacuo (10$^{-3}$ mbar) and subsequently recrystallised.

Method B: Synthesis from Hexafluorophosphates

The hexafluorophosphate peptide linking reagent (4.74 mmol) and potassium tris(pentafluoroethyl)trifluorophosphate, K[(C$_2$F$_5$)$_3$PF$_3$] (2.293 g, 4.74 mmol) are suspended in 20 ml of acetonitrile and stirred at room temperature until a clear solution forms. The acetonitrile is removed in vacuo, and the residue is dried in vacuo (10$^{-3}$ mbar) for two hours. The product is extracted from the residue with the solvent or solvent mixture indicated in Table 1 and subsequently recrystallised.

TABLE 1

Overview of the synthesis methods, denoted by A or B, for the novel amide linking reagents

| Product | Starting material | Method | Solvent or mixture for extraction; amount in ml/mmol | Solvent for the recrystallisation | Yield |
|---|---|---|---|---|---|
| DBTU-FAP | TDBTU | A | — | Dichloromethane/n-hexane | 90% |
| STU-FAP | TSTU | A | — | — | 86% |
| PfTU-FAP | PfTU | B | Dichloromethane; 6 ml/mmol | n-Hexane | 97% |
| OTT-FAP | HOTT | B | Dichloromethane; 3 ml/mmol | Diethyl ether | 82% |
| BTU-FAP | HBTU | B | Dichloromethane with 2% of acetonitrile; 21 ml/mmol | — | 99% |
| BPyU-FAP | HBPyU | B | Dichloromethane; 20 ml/mmol | — | 93% |
| ATU-FAP | HATU | B | Dichloromethane with 2.5% of acetonitrile; 60 ml/mmol | Diethyl ether | 52% |
| BOP-FAP | BOP | B | Dichloromethane; 6 ml/mmol | n-Hexane | 93% |
| PyBOP-FAP | PyBOP | B | Dichloromethane; 4 ml/mmol | n-Hexane | 92% |

TABLE 1-continued

Overview of the synthesis methods, denoted by A or B, for the novel amide linking reagents

| Product | Starting material | Method | Solvent or mixture for extraction; amount in ml/mmol | Solvent for the recrystallisation | Yield |
|---|---|---|---|---|---|
| PyAOP-FAP | PyAOP | B | Dichloromethane; 4.3 ml/mmol | n-Hexane | 100% |
| TFF-FAP | TFFH | B | Dichloromethane; 4.0 ml/mmol | n-Hexane | 99% |
| COMU-FAP | COMU | B | Dichloromethane; 4.6 ml/mmol | n-Hexane | 97% |

Characterisation of the Amide Linking Reagents:

O-(3,4-Dihydro-4-oxo-1,2,3-benzotriazin-3-yl)-N,N,N',N'-tetramethyluronium tris(pentafluoroethyl)trifluorophosphate (DBTU-FAP)

Melting point: 124° C.
Elemental analysis:
experimental, %: N 9.71, C 30.32, H, 2.15;
calculated for $C_{18}H_{16}F_{18}N_5O_2P$, %: N, 9.90, C, 30.56, H, 2.28.
NMR (25° C., solvent: $CD_3CN$; δ in ppm):
$^1$H-NMR: 8.39 (d, d, $^3J_{H,H}$=8.0 Hz, $^4J_{H,H}$=1.4 Hz, 1H), 8.36 (d, m, $^3J_{H,H}$=8.4 Hz, 1H), 8.21 (t, d, $^3J_{H,H}$=7.6 Hz, $^4J_{H,H}$=1.6 Hz, 1H), 8.04 (t, d, $^3J_{H,H}$=7.6 Hz, $^4J_{H,H}$=1.2 Hz, 1H), 3.23 (s, 12H);
$^{13}C\{^1H\}$-NMR: 162.89, 152.34, 144.99, 137.84, 135.23, 130.49, 126.76, 123.16, 41.41:
$^{19}$F-NMR: −44.80 (d, m, $^1J_{F,P}$=890 Hz, 1F, PF), −80.89 (m, 3F, $CF_3$), −82.58 (m, 6F, $2CF_3$), −88.21 (d, m, $^1J_{F,P}$=902 Hz, 2F, PF), −116.27 (br d, $^2J_{F,P}$=82.9 Hz, 2F, $CF_2$), −116.89 (d, m, $^2J_{F,P}$=97.7 Hz, 4F, $2CF_2$):
$^{31}$P-NMR: −147.91 (d, t, t, quin, $^1J_{P,F}$=902 Hz, $^1J_{P,F}$=889.2 Hz, $^2J_{P,F}$=97.4 Hz, $^2J_{P,F}$=83.8 Hz, 1P).
Crystal data: (T=−150° C.): monoclinic, a=10.1170(5) Å, b=15.3535(12) Å, c=16.7415(10) Å, β=91.332(6).

O—(N-Succinimidyl)-N,N,N',N'-tetramethyluronium tris(pentafluoroethyl)trifluorophosphate (STU-FAP)

Melting point: 143° C.
Elemental analysis:
experimental, %: N, 6.19, C, 27.19, H, 2.41;
calculated for $C_{15}H_{16}F_{18}N_3O_3P$, %: N, 6.40, C, 27.33. H, 2.45.
NMR (25° C., solvent: $CD_3CN$; δ in ppm):
$^1$H-NMR: 3.13 (s, 12H), 2.84 (s, 4H);
$^{13}C\{^1H\}$ NMR: 170.90, 163.19, 41.18, 26.59;
$^{19}$F NMR: −44.78 (d, m, $^1J_{F,P}$=890.6 Hz, 1F, PF), −80.86 (m, 3F, $CF_3$), −82.55 (m, 6F, $2CF_3$), −88.20 (d, m, $^1J_{F,P}$=902.2 Hz, 2F, PF), −116.24 (br d, $^2J_{F,P}$=83.0 Hz, 2F, $CF_2$), −116.85 (d, m, $^2J_{F,P}$=97.8 Hz, 4F, $2CF_2$); $^{31}$P NMR: −147.89 (d, t, t, quin, $^1J_{P,F}$=902.3 Hz, $^1J_{P,F}$=889.5 Hz, $^2J_{P,F}$=97.7 Hz, $^2J_{P,F}$=82.9 Hz, 1P).

O-Pentafluorophenyl-N,N,N',N'-tetramethyluronium tris(pentafluoroethyl)trifluorophosphate (PfTU-FAP)

Melting point: 49° C.
Elemental analysis:
experimental, %: N, 3.87, C, 28.05, H, 1.51;
calculated for $C_{17}H_{12}F_{23}N_2OP$, %: N, 3.85, C, 28.04, H, 1.66.
NMR (25° C., solvent: $CD_3CN$; δ in ppm):
$^1$H NMR: 3.12 (s, 12H);
$^{13}C\{^1H\}$: 161.64, 41.24;
$^{19}$F NMR: −44.83 (d, m, $^1J_{F,P}$=889.6 Hz, 1F, PF), −80.93 (m, 3F, $CF_3$), −82.62 (m, 6F, $2CF_3$), −88.23 (d, m, $^1J_{F,P}$=902.3 Hz, 2F, PF), −116.30 (br d, $^2J_{F,P}$=83.2 Hz, 2F, $CF_2$), −116.92 (d, m, $^2J_{F,P}$=97.7 Hz, 4F, $2CF_2$), −157.94 (d, $^3J_{F,F}$=18.2 Hz, 2F, CF), −159.02 (t, $^3J_{F,F}$=21.0 Hz, 1F, CF), −161.55 (d, t, $^3J_{F,F}$=10.4 Hz, $^3J_{F,F}$=10.4 Hz, 2F, CF);
$^{31}$P NMR: −147.89 (d, t, t, quin, $^1J_{P,F}$=902.5 Hz, $^1J_{P,F}$=889.4 Hz, $^2J_{P,F}$=97.6 Hz, $^2J_{P,F}$=83.1 Hz, 1P).

S-(1-Oxido-2-pyridyl)-N,N,N',N'-tetramethylthiouronium tris(pentafluoroethyl)trifluorophosphate (OTT-FAP)

Melting point: 84° C.
Elemental analysis:
experimental, %: N, 6.51, C, 28.79, H, 2.29, S 4.69;
calculated for $C_{16}H_{15}F_{18}N_3OPS$, %: N, 6.27, C, 28.67, H, 2.26, S 4.78.
NMR (25° C., solvent: $CD_3CN$; δ in ppm):
$^1$H NMR: 8.32 (d, d, $^3J_{H,H}$=6.4 Hz, $^4J_{H,H}$=1.2 Hz, 1H), 7.73 (d, d, $^3J_{H,H}$=7.7 Hz, $^4J_{H,H}$=2.2 Hz, 1H), 7.47 (t, d, $3J_{H,H}$=5.9 Hz, $^4J_{H,H}$=2.3 Hz), 7.42 (t, d, $^3J_{H,H}$=7.7 Hz, $^4J_{H,H}$=1.3 Hz, 1H), 3.20 (s, 12H);
$^{13}C\{^1H\}$ NMR: 172.21, 141.27, 131.56, 128.40, 127.53, 44.45;
$^{19}$F NMR ($CD_3CN$, 25° C.): −44.75 (d, m, $^1J_{F,P}$=889.8 Hz, 1F, PF), −80.83 (m, 3F, $CF_3$), −82.52 (m, 6F, $2CF_3$), −88.16 (d, m, $^1J_{F,P}$=902.3 Hz, 2F, PF), −16.21 (br d, $^2J_{F,P}$=83.1 Hz, 2F, $CF_2$), −116.81 (d, m, $^2J_{F,P}$=97.7 Hz, 4F, $2CF_2$); $^{31}$P NMR: −147.87 (d, t, t, quin, $^1J_{P,F}$=902.4 Hz, $J_{P,F}$=889.6 Hz, $^2J_{P,F}$=97.7 Hz, $^2J_{P,F}$=82.8 Hz, 1P).

1-(Dimethylamino(dimethylammonium-1-ylidene)methyl)-1H-benzo[d]-1,2,3-triazole 3-oxide tris(pentafluoroethyl)trifluorophosphate (BTU-FAP)

Melting point: 135° C.
Elemental analysis:
experimental, %: N, 10.03, C, 30.00; H, 2.23;
calculated for $C_{17}H_{16}F_{18}N_5OP$, %: N, 10.31, C, 30.06, H, 2.37.

NMR (25° C., solvent: CD$_3$CN; δ in ppm):

$^1$H NMR: 8.05 (d, t, $^3J_{H,H}$=8.4 Hz, $^4J_{H,H}$=0.9 Hz, 1H), 7.94 (t, t, $^3J_{H,H}$=7.4 Hz, J=1.0 Hz, 1H), 7.71 (d, d, d, $^3J_{H,H}$=8.1 Hz, $^3J_{H,H}$=7.3 Hz, $^4J_{H,H}$=0.5 Hz, 1H), 7.64 (d, m, $^3J_{H,H}$=8.5 Hz, 1H), 3.38 (s, 6H), 3.03 (s, 6H);

$^{13}$C{$^1$H} NMR: 152.14, 134.44, 134.40, 128.43, 117.06, 115.01, 42.96, 42.64.

$^{19}$F NMR: −44.78 (d, m, $^1J_{F,P}$=890.3 Hz, 1F, PF), −80.87 (m, 3F, CF$_3$), −82.57 (br m, 6F, 2CF$_3$), −88.19 (d, m, $^1J_{F,P}$=902.2 Hz, 2F, PF), −116.26 (br d, $^2J_{F,P}$=83.9 Hz, 2F, CF$_2$), −116.85 (d, m, $^2J_{F,P}$=98.3 Hz, 4F, 2CF$_2$);

$^{31}$P NMR: −147.88 (d, t, t, quin, $^1J_{P,F}$=902.1 Hz, $^1J_{P,F}$=889.0 Hz, 2J$_{P,F}$=96.6 Hz, 2J$_{P,F}$=83.8 Hz, 1P).

1-(Pyrrolidino(pyrrolidinium-1-ylidene)methyl)-1H-benzo[d]-1,2,3-triazole 3-oxide tris(pentafluoroethyl)trifluorophosphate (BPyU-FAP)

Melting point: 173° C. (decomposition).

Elemental analysis:

experimental, %: N, 9.58, C, 34.76, H, 2.98;

calculated for C$_{21}$H$_{20}$F$_{18}$N$_5$OP, %: N, 9.58, C, 34.49, H, 2.78.

NMR (25° C., solvent: CD$_3$CN; δ in ppm):

$^1$H NMR: 8.06 (d, $^3J_{H,H}$=8.4 Hz, 1H), 7.94 (d, d, d, $^3J_{H,H}$=8.4 Hz, $^3J_{H,H}$=7.2 Hz, $^4J_{H,H}$=1.0 Hz, 1H), 7.70 (br t, $^3J_{H,H}$=7.7 Hz, 1H), 7.66 (d, $^3J_{H,H}$=8.5, 1H), 3.93 (br m, 4H), 3.67 (very br m, 2H), 3.46 (very br m, 2H), 2.17 (very br m, 4H), 1.99 (very br m, 4H);

$^{13}$C{$^1$H} NMR: 146.27, 134.61, 133.81, 133.44, 128.01, 117.08, 114.35, 54.04 (br), 52.75 (br), 26.91 (br), 25.17 (br);

$^{19}$F NMR: −44.81 (d, m, $^1J_{F,P}$=889.4 Hz, 1F, PF), −80.90 (m, 3F, CF$_3$), −82.60 (m, 6F, 2CF$_3$), −88.21 (d, m, $^1J_{F,P}$=902.3 Hz, 2F, PF), −116.29 (br d, $^2J_{F,P}$=82.0 Hz, 2F, CF$_2$), −116.90 (dm, $^2J_{F,P}$=97.8 Hz, J=8.1 Hz, 4F, 2CF$_2$);

$^{31}$P NMR: −147.92 (d, t, t, quin, $^1J_{P,F}$=903.3 Hz, $^1J_{P,F}$=889.5 Hz, $^2J_{P,F}$=97.5 Hz, $^2J_{P,F}$=83.2 Hz, 1P).

Crystal data: (T=−150° C.): monoclinic, a=8.8373(5) Å, b=31.0766(19) Å, c=10.4906(6) Å, β=110.133(6).

1-(Dimethylamino(dimethylammonium-1-yliden)methyl)-1H-azabenzo-[d][1,2,3]triazole 3-oxide tris(pentafluoroethyl)trifluorophosphate (ATU-FAP)

Melting point: >140° C. (decomposition).

Elemental analysis:

experimental, %: N, 12.27, C, 28.29, H, 2.02;

calculated for C$_{16}$H$_{15}$F$_{18}$N$_6$OP, %: N, 12.35, C, 28.25, H, 2.22.

NMR (25° C., solvent: CD$_3$CN; δ in ppm):

$^1$H NMR: 8.84 (d, d, $^3J_{H,H}$=4.5 Hz, $^4J_{H,H}$=1.1 Hz, 1H), 8.12 (d, d, $^3J_{H,H}$=8.6 Hz, $^4J_{H,H}$=1.3 Hz, 1H), 7.93 (d, d, $^3J_{H,H}$=8.6 Hz, $^4J_{H,H}$=4.5 Hz, 1H), 3.37 (s, 6H), 3.04 (s, 6H);

$^{13}$C{$^1$H} NMR: 152.19, 150.87, 144.97, 128.85, 128.29, 125.00, 43.09, 42.69;

$^{19}$F NMR: −44.80 (d, m, $^3J_{F,P}$=889.5 Hz, 1F, PF), −80.90 (m, 3F, CF$_3$), −82.59 (br m, 6F, 2CF$_3$), −88.21 (d, m, $^3J_{F,P}$=902.2 Hz, 2F, PF), −116.28 (br d, $^2J_{F,P}$=83.0 Hz, 2F, CF$_2$), −116.89 (d, m, $^2J_{F,P}$=97.7 Hz, 4F, 2CF$_2$);

$^{31}$P NMR: −147.88 (d, t, t, quin, J$_{P,F}$=902.6 Hz, J$_{P,F}$=889.2 Hz, $^2J_{P,F}$=98.8 Hz, $^2J_{P,F}$=83.5 Hz, 1P).

(Benzotriazol-1-yloxy)tris(dimethylamino)phosphonium tris(pentafluoroethyl)trifluorophosphate (BOP-FAP)

Melting point: 91° C.

Elemental analysis:

experimental, %: N, 10.99, C, 29.14, H, 3.11;

calculated for C$_{18}$H$_{22}$F$_{18}$N$_6$OP$_2$, %: N, 11.32, C, 29.12, H, 2.99.

NMR (25° C., solvent: CD$_3$CN; δ in ppm):

$^1$H NMR: 8.16 (d, t, $^3J_{H,H}$=8.5 Hz, $^4J_{H,H}$=0.9 Hz, 1H), 7.85-7.75 (m 2H), 7.62 (d, d, d, $^3J_{H,H}$=8.4 Hz, $^3J_{H,H}$=6.5 Hz, $^4J_{H,H}$=1.5 Hz, 1H), 2.84 (d, $^3J_{H,P}$=10.6, 18H);

$^{13}$C{$^1$H} NMR: 144.14, 131.58, 129.01, 127.25, 121.71, 109.27, 38.96 (d, $^2J_{C,P}$=4.3 Hz, CH$_3$).

$^{19}$F NMR: −44.79 (d, m, $^1J_{F,P}$=889.5 Hz, 1F, PF), −80.88 (m, 3F, CF$_3$), −82.57 (m, 6F, 2CF$_3$), −88.20 (d, m, $^1J_{F,P}$=898.5 Hz, 2F, PF), −116.26 (br d, $^2J_{F,P}$=82.8 Hz, 2F, CF$_2$), −116.87 (d, m, $^2J_{F,P}$=97.7 Hz, 4F, 2CF$_2$);

$^{31}$P NMR: 43.67 (m, 1P), −147.91 (d, t, t, quin, $^1J_{P,F}$=902.7 Hz, $^1J_{P,F}$=889.2 Hz, $^2J_{P,F}$=97.5 Hz, $^2J_{P,F}$=83.7 Hz, 1P).

(Benzotriazol-1-yloxy)tris(pyrrolidino)phosphonium tris(pentafluoroethyl)trifluorophosphate (PyBOP-FAP)

Melting point: 66° C.

Elemental analysis:

experimental, %: N, 9.72, C, 34.55, H, 3.30;

calculated for C$_{24}$H$_{28}$F$_{18}$N$_6$OP$_2$, %: N, 10.24, C, 35.13, H, 3.44.

NMR (25° C., solvent: CD$_3$CN; δ in ppm):

$^1$H NMR: 8.12 (d, t, $^3J_{H,H}$=8.5 Hz, $^4J_{H,H}$=0.8 Hz, 1H), 7.80-7.70 (m 2H), 7.59 (d, d, d, $^3J_{H,H}$=8.4 Hz, $^3J_{H,H}$=5.6 Hz, $^4J_{H,H}$=2.4 Hz, 1H), 3.34 (m, 12H), 1.88 (m, 12H);

$^{13}$C{$^1$H} NMR: 144.07 (d, $^4J_{C,P}$=0.4 Hz), 131.29, 128.92 (d, $^3J_{C,P}$=0.9 Hz), 127.16, 121.57, 109.38, 49.24 (d, $^2J_{C,P}$=4.9 Hz), 26.80 (d, $^3J_{C,P}$=9.2 Hz);

$^{19}$F NMR: −44.81 (d, m, $^1J_{F,P}$=889.6 Hz, 1F, PF), −80.90 (m, 3F, CF$_3$), −82.60 (m, 6F, 2CF$_3$), −88.22 (d, m, $^1J_{F,P}$=902.2 Hz, 2F, PF), −116.29 (br d, $^2J_{F,P}$=83.1 Hz, 2F, CF$_2$), −116.90 (d, m, $^2J_{F,P}$=97.8 Hz, 4F, 2CF$_2$);

$^{31}$P NMR: 31.01 (br s, 1P), −147.89 (d, t, t, quin, J$_{P,F}$=902.6 Hz, J$_{P,F}$=889.7 Hz, $^2J_{P,F}$=97.0 Hz, $^2J_{P,F}$=83.7 Hz, 1P).

(7-Azabenzotriazol-1-yloxy)tris(pyrrolidino)phosphonium tris(pentafluoroethyl)trifluorophosphate (PyAOP-FAP)

Melting point: 77° C.

Elemental analysis: experimental, %: N, 11.77, C, 33.68, H, 3.39;

calculated for C$_{23}$H$_{27}$F$_{18}$N$_7$OP$_2$, %: N, 11.94, C, 33.63, H, 3.31.

NMR (25° C., solvent: CD$_3$CN; δ in ppm):

$^1$H NMR: 8.84 (d, $^3J_{H,H}$=4.5 Hz, 1H), 8.54 (d, $^3J_{H,H}$=8.4 Hz, 1H), 7.62 (d, d, $^3J_{H,H}$=8.4 Hz, $^3J_{H,H}$=5.6 Hz, 1H), 3.37 (m, 12H), 1.88 (m, 12H); $^{13}$C{$^1$H} NMR: 154.25, 141.05, 135.92, 131.17, 123.32, 49.26 (d, $^2J_{C,P}$=4.5 Hz), 26.84 (d, $^3J_{C,P}$=9.3 Hz);

$^{19}$F NMR: −44.78 (d, m, $^1J_{F,P}$=889.7 Hz, 1F, PF), −80.85 (m, 3F, CF$_3$), −82.54 (m, 6F, 2CF$_3$), −88.17 (d, m, $^1J_{F,P}$=902.4 Hz, 2F, PF), −116.24 (br d, $^2J_{F,P}$=82.7 Hz, 2F, CF$_2$), −116.85 (d, m, $^2J_{F,P}$=97.7 Hz, 4F, 2CF$_2$);

$^{31}$P NMR: 30.93 (br s, 1P), −147.90 (d, t, t, quin, $^1J_{P,F}$=902.4 Hz, $^1J_{P,F}$=889.6 Hz, $^2J_{P,F}$=97.7 Hz, $^2J_{P,F}$=83.1 Hz, 1P).

Fluoro-N,N,N',N'-tetramethylformamidinium tris(pentafluoroethyl)-trifluorophosphate (TFF-FAP)

Melting point: 82° C.
Elemental analysis: experimental, %: N, 4.92, C, 23.48, H, 2.14;
calculated for $C_{11}H_{12}F_{19}N_2P$, %: N, 4.97, C, 23.42, H, 2.14.
NMR (25° C., solvent: $CD_3CN$; δ in ppm):
$^1$H NMR: 3.16 (d, $^4J_{H,F}$=3.0 Hz, 12H);
$^{13}C\{^1H\}$ NMR: 120.13 (m, $^1J_{C,F}$=285.2 Hz), 49.26 (d, $^2J_{C,F}$=4.5 Hz), 26.84 (d, $^3J_{C,P}$=9.3 Hz), 39.11;
$^{19}$F NMR: −44.77 (d, m, $^1J_{F,P}$=889.5 Hz, 1F, PF), −45.17 (tridecet, $^4J_{F,H}$=3.0 Hz, 1F, CF), −80.92 (m, 3F, $CF_3$), −82.61 (m, 6F, $2CF_3$), −88.25 (d, m, $^1J_{F,P}$=904.2 Hz, 2F, PF), −116.34 (br d, $^2J_{F,P}$=82.3 Hz, 2F, $CF_2$), −116.92 (d, m, $^2J_{F,P}$=97.7 Hz, 4F, $CF_2$);
$^{31}$P NMR: −147.90 (d, t, t, quin, $^1J_{P,F}$=904.2 Hz, $J_{P,F}$=889.5 Hz, $^2J_{P,F}$=97.7 Hz, $^2J_{P,F}$=82.3 Hz, 1P).

(1-Cyano-2-ethoxy-2-oxoethylideneaminooxy)dimethylaminomorpholinocarbenium tris(pentafluoroethyl)trifluorophosphate (COMU-FAP)

Melting point: 79° C.
Elemental analysis: experimental, %: N, 7.69, C, 29.63, H, 2.44;
calculated for $C_{18}H_{19}F_{18}N_4O_4P$, %: N, 7.69, C, 29.68, H, 2.63.
NMR (25° C., solvent: $CD_3CN$; δ in ppm):
$^1$H NMR: 4.49 (q, $^3J_{H,H}$=7.1 Hz, 2H, $CH_2$), 3.82 (t, $^3J_{H,H}$=4.7 Hz, 4H, $CH_2$), 3.56 (t, $^3J_{H,H}$=4.7 Hz, 4H, $CH_2$), 3.19 (s, 6H, $CH_3$), 1.40 (t, $^3J_{H,H}$=7.1 Hz, 2H, $CH_3$);
$^{13}C\{^1H\}$ NMR: 159.82, 155.47, 134.43, 106.05, 65.36, 64.65, 49.36, 40.25, 12.84;
$^{19}$F NMR: −44.83 (d, m, $^1J_{F,P}$=889.2 Hz, 1F, PF), −80.86 (m, 3F, $CF_3$), −82.56 (m, 6F, $2CF_3$), −88.26 (d, m, $^1J_{F,P}$=901.8 Hz, 2F, PF), −116.24 (br d, $^2J_{F,P}$=83.1 Hz, 2F, $CF_2$), −116.87 (d, m, $^2J_{F,P}$=98.2 Hz, 4F, $2CF_2$);
$^{31}$P NMR: −147.92 (d, t, t, quin, $^1J_{P,F}$=901.8 Hz, $^1J_{P,F}$=889.6 Hz, $^2J_{P,F}$=98.2 Hz, $^2J_{P,F}$=83.1 Hz, 1P).

Example B) Solubility of the Amide Linking Reagents

All solubility determinations are carried out in a tared gas-tight 4 ml bottle with magnetic stirrer bar. The amide linking reagent (at least 5 mg) is weighed out and a certain amount of the solvent to be investigated is added. The mixture is stirred for 2-5 minutes. If undissolved solid is still present, solvent (50-100 μl) is additionally added, and the mixture is stirred again. As soon as a clear solution is present, the experiment is terminated. Table 2 below summarises the solubilities of the peptide linking reagents investigated.

TABLE 2 solubilities of the amide linking reagents in mg/ml; FAP⁻ in Table 2 denotes $[(C_2F_5)_3PF_3]^-$

| Reagent | $CH_2Cl_2$ | $CH_3CN$ | $9CH_2Cl_2$:1$CH_3CN$ | THF | DMF |
|---|---|---|---|---|---|
| HDBTU | 3.75 | 240 | 17 | <3.3 | 250 |
| DBTU-FAP | >780 | >860 | 480 | >780 | >1125 |
| TSTU | <1.2 | 265 | 2.9 | <1.2 | 220 |
| STU-FAP | 3.0 | >2000 | 110 | 690 | >2000 |
| PfTU | <1.2 | 1000 | 2.5 | <1.2 | 1000 |
| PfTU-FAP | 1000 | >2000 | >2000 | 1000 | >2000 |
| HOTT | 59 | 810 | 180 | <1.2 | 690 |
| OTT-FAP | 690 | >2000 | >2000 | 1400 | >2000 |
| HBTU | <1.1 | 124 | <2.8 | <3.6 | 200 |
| BTU-FAP | 6.9 | >1040 | 120 | 364 | >1200 |
| HBPyU | 68.3 | 510 | 118 | <3.3 | 540 |
| BPyU-FAP | 57 | >1020 | 190 | 510 | >1100 |
| HATU | <1.2 | 212 | 1.2 | <1.2 | 370 |
| ATU-FAP | <1.2 | >2000 | 67 | 670 | >2000 |
| BOP | >380 | 510 | >335 | <4.2 | 660 |
| BOP-FAP | >1040 | >700 | >800 | >1200 | >1100 |
| PyBOP | 680 | 830 | 660 | 4.3 | 670 |
| PyBOP-FAP | >1650 | >1550 | >1500 | >1500 | >1550 |
| PyAOP | 1000 | 1000 | 670 | 6.0 | 670 |
| PyAOP-FAP | >2000 | >2000 | >2000 | >2000 | >2000 |
| TFFH | 220 | 1360 | 595 | 6.3 | 610 |
| TFF-FAP | 1190 | 4490 | >2000 | 880 | >2000 |
| COMU | 82 | 565 | 294 | 4.1 | 530 |
| COMU-FAP | 180 | 905 | >2000 | 349 | >1500 |

| Reagent | Hexane | Toluene |
|---|---|---|
| HDBTU | <1.2 | <1.2 |
| DBTU-FAP | <1.2 | <1.2 |
| TSTU | <1.2 | <1.2 |
| STU-FAP | <1.2 | <1.2 |
| PfTU | <1.2 | <1.2 |
| PfTU-FAP | <1.2 | <1.2 |
| HOTT | <1.2 | <1.2 |
| OTT-FAP | <1.2 | <1.2 |
| HBTU | <1.2 | <1.2 |
| BTU-FAP | <1.2 | <1.2 |
| HBPyU | <1.2 | <1.2 |
| BPyU-FAP | <1.2 | <1.2 |
| HATU | <1.2 | <1.2 |
| ATU-FAP | <1.2 | <1.2 |
| BOP | <1.2 | <1.2 |
| BOP-FAP | <1.2 | <1.2 |
| PyBOP | <1.2 | <1.2 |
| PyBOP-FAP | <1.2 | 5.0 |
| PyAOP | <1.2 | <1.2 |
| PyAOP-FAP | <1.2 | b |
| TFFH | 2.2 | 4.8 |
| TFF-FAP | 6.2 | 13.1 |
| COMU | <1.2 | 3.2 |
| COMU-FAP | 2.1 | 4.5 | b means that the formation of two liquid phases was observed

The solubility in the nonpolar solvents hexane and toluene is as expected virtually unchanged, since these are still ionic compounds. However, the tendency of the solubility improvement on comparison of TFFH and TFF-FAP and COMU and COMU-FAP is evident.

Example C) Activation Experiments with Z-Aib-OH

Z-Aib-OH (N-benzyloxycarbonyl-α-aminoisobutyric acid) was selected for the activation experiments since it carries a carboxyl group which is not easy to activate, as mentioned above. In a typical experiment, two equivalents of TMP are added to a 0.1 M solution of Z-Aib-OH in THF with one equivalent of amide linking reagent. ~20 μl of the reaction mixture are removed at certain time intervals (4, 20 and 40 minutes) and dissolved in 0.6-0.7 ml of deuterated chloroform in an NMR tube. The samples are cooled at 00° C. until the NMR-spectroscopic investigation (for about 20-25 minutes). The intensities of the benzyl proton NMR signals of the acid (5.05 ppm) and of the active ester (~5.20 ppm) are compared with one another in order to calculate the reaction conversion [L. A. Carpino, A. El-Faham, *J. Org. Chem.* 1994, 59, 695-698]. All results are summarised in Table 3.

TABLE 3

Activation of Z-Aib-OH by the amide linking reagents shown in the table

| Reagent | Time | Conversion, % for X⁻ = $BF_4^-$ | Conversion, % for X⁻ = $[(C_2F_5)_3PF_3]^-$ |
|---|---|---|---|
| 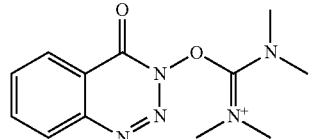 | 4 minutes<br>20 minutes<br>40 minutes | 6<br>36<br>62 | 90<br>95<br>99 |
| 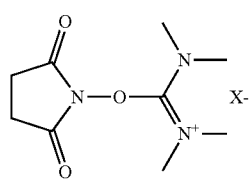 | 4 minutes<br>20 minutes<br>40 minutes | 0<br>0<br>0 | 26<br>50<br>63 |

| Reagent | Time | Conversion, % for X⁻ = $PF_6^-$ | Conversion, % for X⁻ = $[(C_2F_5)_3PF_3]^-$ |
|---|---|---|---|
| 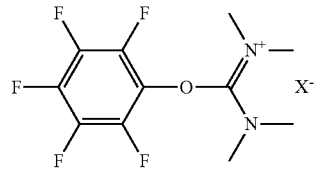 | 4 minutes<br>20 minutes<br>40 minutes | 52<br>80<br>87 | 91<br>95<br>97 |
| 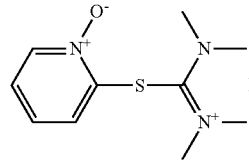 | 4 minutes<br>20 minutes<br>40 minutes | 3.7<br>3.7<br>4.0 | 8<br>15<br>21 |
| 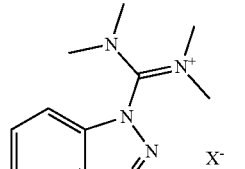 | 4 minutes<br>20 minutes<br>40 minutes | 3<br>2<br>4 | 79<br>89<br>95 |
| 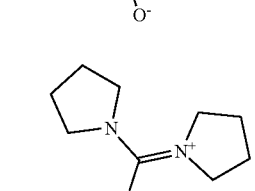 | 4 minutes<br>20 minutes<br>40 minutes | 11<br>21<br>24 | 87<br>97<br>97 |

TABLE 3-continued

Activation of Z-Aib-OH by the amide linking reagents shown in the table

| Reagent | Time | Value 1 | Value 2 |
|---|---|---|---|
| (HATU-type, X⁻) | 4 minutes | 0 | 100 |
| | 20 minutes | 0 | 100 |
| | 40 minutes | 6 | 100 |
| (BOP-type, X⁻) | 4 minutes | 7 | 28 |
| | 20 minutes | 22 | 64 |
| | 40 minutes | 43 | 76 |
| (PyBOP-type, X⁻) | 4 minutes | 31 | 53 |
| | 20 minutes | 65 | 83 |
| | 40 minutes | 82 | 88 |
| (PyAOP-type, X⁻) | 4 minutes | 62 | 71 |
| | 20 minutes | 89 | 90 |
| | 40 minutes | 93 | 93 |

The activation of the acid and thus also the further steps of the amide bond formation in most cases proceeds faster with the amide linking reagents containing the anion [(C$_2$F$_5$)$_3$F$_3$P]$^-$. The acceleration of the activation is less pronounced for the amide linking reagents PyBOP-FAP and PyAOP-FAP.

Example D) Synthesis of Ac-Phe-Ala-OMe

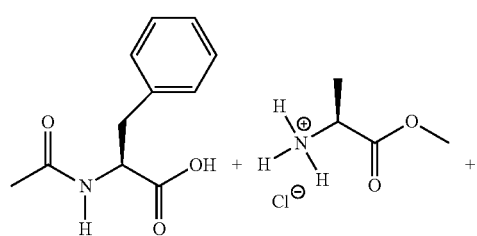

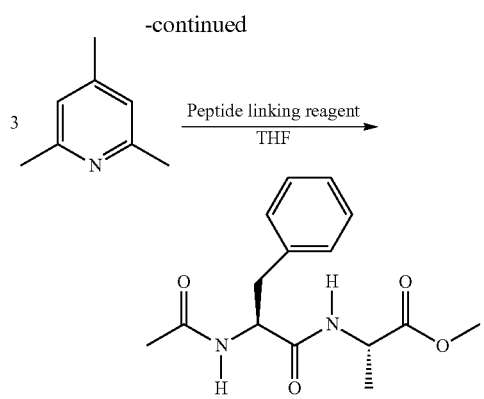

In this reaction, not only the conversion, but also the degree of epimerisation can easily be analysed with the aid of $^1$H NMR spectroscopy [B. Weinstein, A. E. Pritchard, *J. Chem. Soc., Perkin Trans.* 1 1972, 1015].

In a typical experiment, three equivalents of TMP (collidine) are added to an Ac-Phe-OH solution (Ac-Phe-OH=acetyl-protected phenylalanine) in THF (0.2 M) with one equivalent of Ala-OMe hydrochloride (Ala-OMe=alanine methyl ester) and one equivalent of peptide linking reagent. At certain time intervals (5, 10 and 15 minutes), 40 μl of the mixture are dissolved in 0.6-0.7 ml of acetonitrile-$d_3$ in an NMR tube and cooled at 0° C. When all three samples have been prepared, $^1$H NMR spectra of these samples are measured at 25° C. In these spectra, the doublet of the alanine methyl group is at δ=1.32 ppm in the dipeptide and at δ=1.25 ppm in the epimer, the doublet of unreacted Ala-OMe hydrochloride is in the range δ=1.40-1.50 ppm. The conversion and the degree of epimerisation of the dipeptide is calculated by integration of three signals. The results for the conversion are summarised in Table 4 and the results for the degree of epimerisation are summarised in Table 5.

TABLE 5

| Reagent | Time | Conversion, % for $X^-$ = $BF_4^-$ | Conversion, % for $X^-$ = $[(C_2F_5)_3PF_3]^-$ |
| --- | --- | --- | --- |
| 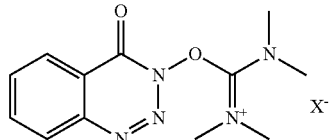 | 5 minutes<br>10 minutes<br>15 minutes | 74<br>89<br>94 | 100<br>100<br>100 |
| 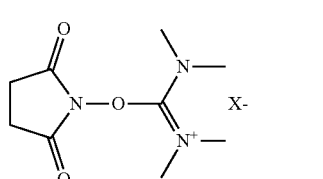 | 5 minutes<br>10 minutes<br>15 minutes | 9<br>11<br>20 | 41<br>55<br>67 |

| Reagent | Time | Conversion, % for $X^-$ = $PF_6^-$ | Conversion, % for $X^-$ = $[(C_2F_5)_3PF_3]^-$ |
| --- | --- | --- | --- |
| 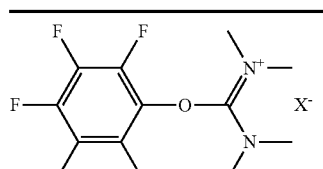 | 5 minutes<br>10 minutes<br>15 minutes | 32<br>55<br>68 | 44<br>63<br>73 |
| 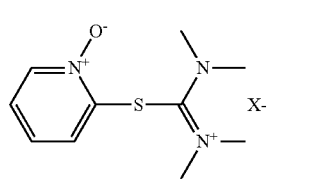 | 5 minutes<br>10 minutes<br>15 minutes | 0<br>1.7<br>2 | 5<br>13<br>19 |
| 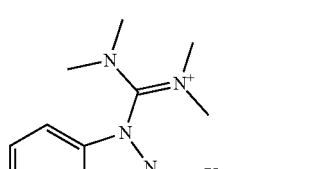 | 5 minutes<br>10 minutes<br>15 minutes | 5.3<br>6<br>6.3 | 93<br>100<br>100 |
| 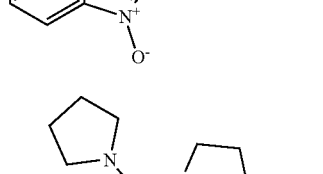 | 5 minutes<br>10 minutes<br>15 minutes | 49<br>69<br>76 | 100<br>100<br>100 |

TABLE 5-continued

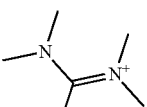

| | 5 minutes | 58 | 100 |
| | 10 minutes | 69 | 100 |
| | 15 minutes | 76 | 100 |

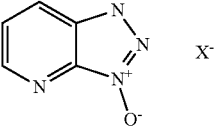

| | 5 minutes | 44 | 67 |
| | 10 minutes | 59 | 77 |
| | 15 minutes | 68 | 80 |

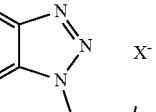

| | 5 minutes | 71 | 85 |
| | 10 minutes | 83 | 91 |
| | 15 minutes | 87 | 94 |

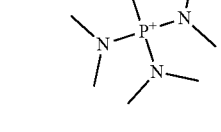

| | 5 minutes | 90 | 92 |
| | 10 minutes | 97 | 100 |
| | 15 minutes | 100 | 100 |

The conversions are calculated from the integrals of the alanine methyl group of Ala-OMe, dipeptide and epimer.

An accelerated reaction is observed in the case of all amide linking reagents. The advantage of the novel peptide linking reactions is, in particular, the gain in time in the peptide synthesis through faster reaction times.

The results for the degree of epimerisation are summarised in Table 5.

TABLE 5

| Reagent | Time | Epimerisation, % for $X^- = BF_4^-$ | Epimerisation, % for $X^- = [(C_2F_5)_3PF_3]^-$ |
|---|---|---|---|
| 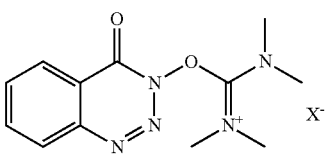 | 5 minutes | 0 | 0 |
| | 10 minutes | 0 | 0 |
| | 15 minutes | 0.6 | 0.4 |

TABLE 5-continued

| Reagent | Time | Epimerisation, % for X⁻ = PF₆⁻ | Epimerisation, % for X⁻ = [(C₂F₅)₃PF₃]⁻ |
|---|---|---|---|
| (N-hydroxysuccinimide tetramethyluronium structure) | 5 minutes | b | 4.0 |
| | 10 minutes | b | 4.0 |
| | 15 minutes | 3.8 | 5.1 |
| (pentafluorophenoxy tetramethyluronium structure) | 5 minutes | 3.9 | 6.2 |
| | 10 minutes | 6.0 | 9.0 |
| | 15 minutes | 8.1 | 9.9 |
| (2-pyridyl N-oxide thio tetramethyluronium structure) | 5 minutes | b | b |
| | 10 minutes | b | 9.1 |
| | 15 minutes | b | 9.1 |
| (benzotriazole N-oxide tetramethyluronium structure, HBTU-like) | 5 minutes | b | 3.1 |
| | 10 minutes | b | 2.8 |
| | 15 minutes | b | 3.2 |
| (benzotriazole N-oxide dipyrrolidino structure) | 5 minutes | 8.2 | 3.3 |
| | 10 minutes | 7.3 | 1.8 |
| | 15 minutes | 5.0 | 2.4 |
| (azabenzotriazole N-oxide tetramethyluronium structure, HATU-like) | 5 minutes | 0 | 1.6 |
| | 10 minutes | 1.0 | 1.2 |
| | 15 minutes | 1.0 | 1.4 |
| (benzotriazolyloxy tris(dimethylamino)phosphonium structure, BOP-like) | 5 minutes | 3.5 | 1.9 |
| | 10 minutes | 3.9 | 3.0 |
| | 15 minutes | 4.2 | 3.4 |

TABLE 5-continued

| | 5 minutes | 2.2 | 2.4 |
|---|---|---|---|
| | 10 minutes | 2.8 | 2.3 |
| | 15 minutes | 3.1 | 2.4 |
| | 5 minutes | 0.7 | 0.9 |
| | 10 minutes | 0.7 | 0.6 |
| | 15 minutes | 0.8 | 1.0 |

If the letter b is used in the table, it was not possible to calculate the degree of epimerisation owing to inadequate intensity of the signal.

In some cases, a reduction in the degree of epimerisation is observed.

The invention claimed is:

1. A process for production of an amide bond comprising:

reacting an acid with a primary or secondary amine in the presence of a base with the aid of at least one amide linking reagent, wherein said at least one amide linking reagent contains an anion of formula (I), $$[P(C_nF_{2n+1})_yF_{6-y}]^- \quad (I),$$

where n stands on each occurrence, independently, for 1, 2, 3, 4, 5, 6, 7 or 8 and y stands for 1, 2, 3 or 4.

2. The process according to claim 1, wherein n stands on each occurrence, independently, for 2, 3 or 4.

3. The process according to claim 1, wherein said anion of the formula (I) is selected from $[(C_2F_5)_3PF_3]^-$, $[(C_3F_7)_3PF_3]^-$, $[(C_4F_9)_3PF_3]^-$, $[(C_2F_5)_2PF_4]^-$, $[(C_3F_7)_2PF_4]^-$, $[(C_4F_9)_2PF_4]^-$, $[(C_2F_5)PF_5]^-$, $[(C_3F_7)PF_5]^-$ and $[(C_4F_9)PF_5]^-$.

4. The process according to claim 1, wherein the cation of said at least one amide linking reagent is a uronium, thiouronium, guanidinium, aminium, carbonium, imidazolium or phosphonium cation.

5. The process according to claim 1, wherein a peptide bond is produced.

6. A compound selected from the following group of compounds;

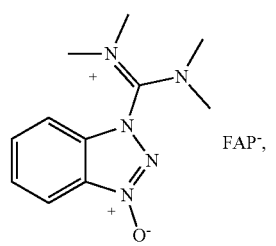

FAP⁻,

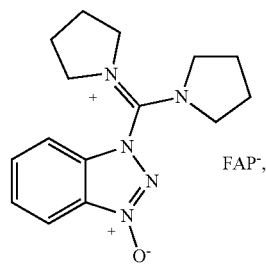

FAP⁻,

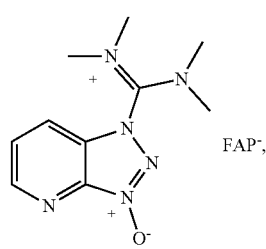

FAP⁻,

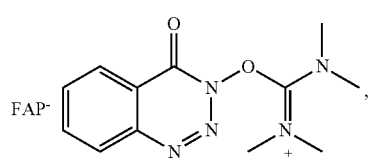

FAP⁻,

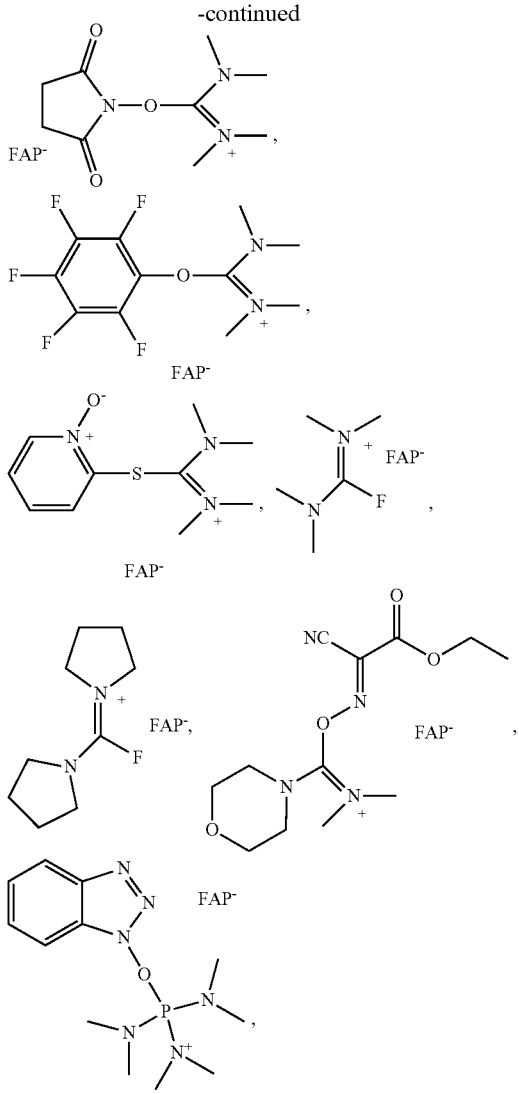
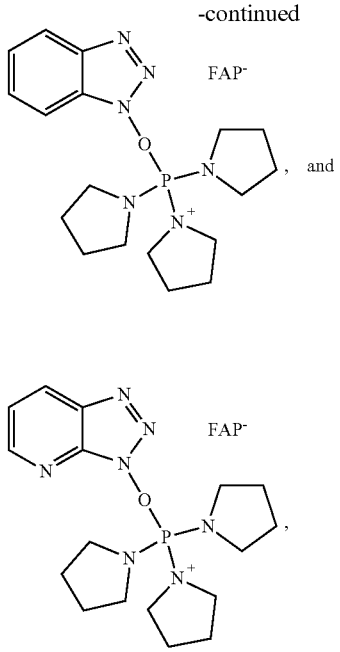
wherein FAP stands for an anion of the following formula (I),
$$[P(C_nF_{2n+1})_yF_{6-y}]^- \qquad (I),$$
where
n stands on each occurence, independently, for 1, 2, 3, 4, 5, 6, 7 or 8, and
y stands for 1, 2, 3 or 4.
7. A compound according to claim 6, where FAP⁻ stands for $[(C_2F_5)_3PF_3]^-$ or $[(n\text{-}C_4F_9)_3PF_3]^-$.
* * * * *